(12) United States Patent
Berry (10) Patent No.: US 7,741,506 B2
(45) Date of Patent: Jun. 22, 2010

(54) PROBE FOR MEASURING PHYTASE ACTIVITY

(75) Inventor: David A. Berry, Ann Arbor, MI (US)

(73) Assignee: Berry & Associates, Inc., Dexter, MI (US)

( * ) Notice: Subject to any disclaimer, the term of this patent is extended or adjusted under 35 U.S.C. 154(b) by 423 days.

(21) Appl. No.: 11/982,811

(22) Filed: Nov. 5, 2007

(65) Prior Publication Data

US 2008/0132713 A1 Jun. 5, 2008

Related U.S. Application Data

(63) Continuation-in-part of application No. 11/249,231, filed on Oct. 13, 2005, now abandoned.

(60) Provisional application No. 60/674,950, filed on Apr. 26, 2005.

(51) Int. Cl.
C07F 9/28 (2006.01)
C07F 9/655 (2006.01)

(52) U.S. Cl. .................. 558/158; 564/186; 562/20; 549/220

(58) Field of Classification Search ............ 558/158; 549/220; 564/186; 562/20
See application file for complete search history.

(56) References Cited

U.S. PATENT DOCUMENTS

2004/0106158 A1 6/2004 Naqvi et al.

OTHER PUBLICATIONS

Riley et al., Journal of Biological Chemistry, vol. 277, No. 43, 2002, 40290-40295.*
Berry and Berry. Tethered phytic acid as a probe for measuring phytase activity. Bioorganic & Medicinal Chemistry Letters 15 (2005) 3157-3161.
Marecek and Prestwich. Synthesis of Tethered Phytic Acid. Tetrahedron Letters vol. 32 No. 16pp. 1863-1866, 1991.
Glenn D. Presiwich. Tethered IP3. Syntesis and Biochemical Applications of the 1-0-(3-Aminopropyl)Ester of Inositol, 1,4,5-Trisphosphate, J. Am. Chem. Soc. 1991. 1822-1825.
Jeroni Morey. A 'naked eye' chemosensor system for phytate, Tetrahedron Letters 45 2004, 121-1265, Elsevier Ltd.
Shoichiro Ozaki. Synthesis and Some Properties of D-myo-Inositol 1,4,5-Tris (dihydrogen phosphate), J. Chem. Soc. Perkin Trans., 1992, 729-737.

J. Garegg. Synthesis of some mono-O-benzyl-and penta-O-methyl-myo-Inositols*. Carbohydrate Research, 1984, 322-326, Elsevier Science Publishers B.V., Amsterdam.
James F. Marecek. Synthesis of Tethered Phytic Acid. Tetrahedron Letters, 1991, 1863-1866, vol. 32, No. 16.
Wikipedia. Inositol triphosphate, [online], [retrieved on Jan. 22, 2007], retrieved from the Internet <url:http://en.wikipedia.org/wik/Inositol_triphosphate).
Andrew M. Riley. Dimers of D-myo-Inositol 1,4,5-Trisphosphate: Design, Synthesis, and Interaction with Ins(1,4,5) P3 Receptors, Bioconjugate Chem., 2004, 278-289, 15, American Chemical Society.

* cited by examiner

Primary Examiner—Shailendra Kumar
(74) Attorney, Agent, or Firm—Young Basile Hanlon & MacFarlane, P.C.

(57) ABSTRACT

A myo-inositol derivative:

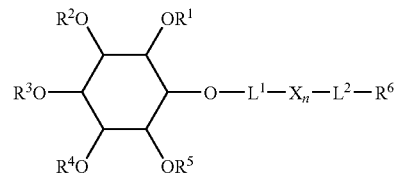

$R^1$, $R^2$, $R^3$ and $R^4$ are identical, being selected from $PO_3H_2$, $PO_3Na_2$, $PO_3K_2$, $PO_3Li_2$, $PO_3Ca$, $PO_3Mg$, $PO_3(NH_4)_2$, $PO_3(RNH_3)_2$, $PO_3(R_2NH_2)_2$, $PO_3(R_4N)_2$, $PO(OR)_2$, H, COZ and BHPP, where R is benzyl or alkyl of 1 to 6 carbon atoms and Z is an alkyl or arylalky group providing a cleavable protecting group; $R^5$ is one of H, benzyl, 4-methoxybenzyl, COZ, $PO_3H_2$, $PO_3Na_2$, $PO_3K_2$, $PO_3Li_2$, $PO_3Ca$, $PO_3Mg$, $PO_3(NH_4)_2$, $PO_3(RNH_3)_2$, $PO_3(R_2NH_2)_2$, $PO_3(R_4N)_2$, $PO(OR)_2$, and BHPP, where R is benzyl or alkyl of 1 to 6 carbon atoms and Z is an alkyl or arylalky group providing a cleavable protecting group; X is one of $CH_2$, $CH_2CH_2O$, and $CH_2CH_2CH_2O$; n is an integer from 1 to 8; $L^1$ is a single bond or $CH_2$; $L^2$ is one of a single bond, CONH, $CH_2CONH$, $CH_2CH_2CONH$, $CH_2CH_2NHCO$, $CH_2CH_2NHCONH$, $CH_2CH_2NHCSNH$, $CH_2CH_2NHSO_2$, $CH_2CH_2CH_2NHCO$, $CH_2CH_2CH_2NHCONH$, $CH_2CH_2CH_2NHCSNH$, $CH_2CH_2CH_2NHSO_2$, NHCO, NHCONH, NHCSNH, OCONH, $CH_2$, $CH_2CH_2$, $CH_2CH_2O$, $CH_2CH_2S$, $CH_2CH_2NH$, $CH_2CH_2CH_2$, $CH_2CH_2CH_2O$, $CH_2CH_2CH_2S$, $CH_2CH_2CH_2NH$, and $NH-SO_2$; and $R^6$ is a UV-visible chromophore, a UV-chromophore, a fluorescent moiety, or a radiolabeled moiety.

19 Claims, 4 Drawing Sheets

PROBE FOR MEASURING PHYTASE ACTIVITY

CROSS-REFERENCE TO RELATED APPLICATIONS

This application is a continuation-in-part of, and claims the benefit of priority from, U.S. patent application Ser. No. 11/249,231, filed Oct. 13, 2005, now abandoned, which application claims the benefit of priority from U.S. Provisional Patent Application Ser. No. 60/674,950, filed Apr. 26, 2005. The entire contents of the foregoing cases are incorporated herein by reference in their entireties.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

FIELD OF THE INVENTION

The present invention pertains to probes for measuring phytase activity, and more particularly to such probes comprising a myo-inositol derivative compound of the following nominal formula:

BACKGROUND

The majority of phosphorous (P) in farm animal feed grains is present as a mixed salt of myo-inositol hexakisphosphate, shown below, and more commonly referred to as phytic acid ("myo-$IP_6$").

Phytic Acid (myo-$IP_6$)

Because grain-consuming animals such as swine and poultry do not produce the enzyme phytase, myo-$IP_6$ is largely unavailable as a phosphorus-containing nutrient source and is thus excreted in high concentrations in the waste of these animals. Such waste is, however, applied to croplands as a means of enhancing soil fertility, though little information exists regarding the process of how myo-$IP_6$ is transformed into a crop-available nutrient. At least in part, this lack of information respecting the fate of myo-$IP_6$ in soil and water-sediment environments is attributable to the absence of artificial substrates that can be used for the convenient measurement of phytase activity. Still, recent experimental evidence suggests that bacterial phytase plays an important role in the (bio)chemical transformation.

Phytases catalyze the sequential hydrolysis of myo-$IP_6$, forming orthophosphate (ortho-P) and a series of partially dephosphorylated phosphoric esters of myo-inositol. In some cases, hydrolysis may go to completion yielding the parent compound myo-inositol. Based on biochemical properties of the amino acid sequence alignment, others have characterized phytases into two major classes, the histidine acid phytases (comprising the PhyA, PhyB, and PhyC groups), to which most of the bacterial and fungal phytases belong, and the alkaline phytases (PhyD). The phytate-degrading enzyme, 3-phytase (myo-inositol hexakisphosphate 3-phosphohydrolase, EC 3.1.3.8; PhyA and PhyB groups) hydrolyzes myo-$IP_6$ preferentially at the C-3 position, while 6-phytase (myo-inositol hexakisphsophate 6-phosphohydrolase, EC 3.1.3.26; PhyC) hydrolyzes myo-$IP_6$ preferentially at the C-6 position.

Conventional phytase assays conducted on bacterial cell wall-free lysate or whole cell lysate routinely call for the addition of myo-$IP_6$ to buffered cell lysate and subsequent measurement of the released ortho-P by colorimetric analysis. However, experiments by the inventor hereof demonstrates substantial ortho-P release from bacterial cell lysate resulting from "cell free" phosphate-mediated hydrolysis of cell-associated phosphate compounds, including accumulated intracellular polyphosphate. Notably, bacteria, archaea and fungi are all capable of producing polyphosphate. Thus, it would seem that the conventional ortho-P release assay is not a specific measure of phytase activity in lysed cell preparations, and its use under such conditions may result in an exaggerated estimate of phytase activity or, possibly, even a false positive test result.

In light of the foregoing, it would be desirable to provide a specific and sensitive quantitative enzyme assay capable of measuring phytase activity in cell culture filtrates, cell-lysate preparations, soils, etc.

SUMMARY OF THE INVENTION

The specification discloses a myo-inositol derivative compound characterized by the following nominal formula:

Wherein $R^1$, $R^2$, $R^3$ and $R^4$ are identical and are selected from the group consisting of $PO_3H_2$, $PO_3Na_2$, $PO_3K_2$, $PO_3Li_2$, $PO_3Ca$, $PO_3Mg$, $PO_3(NH_4)_2$, $PO_3(RNH_3)_2$, $PO_3(R_2NH_2)_2$, $PO_3(R_4N)_2$, $PO(OR)_2$, H, COZ and BHPP, where R is benzyl or alkyl of 1 to 6 carbon atoms and Z is an alkyl or arylalky group that provides a cleavable ester protecting group; $R^5$ is selected from the group consisting of H, benzyl, 4-methoxybenzyl, COZ, $PO_3H_2$, $PO_3Na_2$, $PO_3K_2$, $PO_3Li_2$, $PO_3Ca$, $PO_3Mg$, $PO_3(NH_4)_2$, $PO_3(RNH_3)_2$, $PO_3(R_2NH_2)_2$, $PO_3(R_4N)_2$, $PO(OR)_2$, and BHPP, where R is benzyl or alkyl of 1 to 6 carbon atoms and Z is an alkyl or arylalky group that provides a cleavable ester protecting group; X is selected from the group consisting of $CH_2$, $CH_2CH_2O$, and $CH_2CH_2CH_2O$; n is an integer from 1 to 8; $L^1$ is selected from the group consisting of a single bond and $CH_2$; $L^2$ is selected from the group consisting of a single bond, CONH, $CH_2CONH$, $CH_2CH_2CONH$, $CH_2CH_2CONH$, $CH_2CH_2CONH$, $CH_2CH_2NHCONH$, $CH_2CH_2NHCSNH$, $CH_2CH_2NHSO_2$, $CH_2CH_2CH_2NHCO$, $CH_2CH_2CH_2NHCONH$, $CH_2CH_2CH_2NHCSNH$, $CH_2CH_2CH_2NHSO_2$, NHCO, NHCONH, NHCSNH, OCONH, $CH_2$, $CH_2CH_2$, $CH_2CH_2O$, $CH_2CH_2S$, $CH_2CH_2NH$, $CH_2CH_2CH_2$, $CH_2CH_2CH_2O$, $CH_2CH_2CH_2S$, $CH_2CH_2CH_2NH$, and $NH-SO_2$; and $R^6$ is selected from the group consisting of UV-visible chromophores, UV-chromophores, fluorescent moieties, and radiolabeled moieties.

According to another embodiment of this derivative compound, $R^1$, $R^2$, $R^3$, $R^4$ and $R^5$ are selected from the group consisting of $PO_3H_2$, $PO_3Na_2$, $PO_3(NH_4)_2$, and BHPP, X is $CH_2$ or $CH_2CH_2O$, n is an integer from 2 to 8, $L^1$ is a single bond or is $CH_2$, $L^2$ is selected from the group consisting of a single bond, CONH, NHCO, NHCONH, NHCSNH, OCONH, $NHSO_2$, $CH_2CH_2CONH$, $CH_2CH_2CH_2NH$, $CH_2CH_2CH_2NHCO$, $CH_2CH_2CH_2NHCONH$, $CH_2CH_2CH_2NHCSNH$, $CH_2CH_2CH_2OCONH$, and $CH_2CH_2CH_2NHSO_2$, and $R^6$ is selected from the group consisting of UV-visible chromophores, UV-chromophores, fluorescent moieties, and radiolabeled moieties. In one variation, $R^6$ is selected from the group consisting of UV-chromophores and fluorescent moieties. In a further variation of this embodiment, X is $CH_2$, n is 6, and $L^2$ is selected from the group consisting of NH—CO and NH—CS—NH.

According to another embodiment, $R^1$, $R^2$, $R^3$, $R^4$ and $R^5$ are selected from the group consisting of $PO_3H_2$, $PO_3Na_2$, $PO_3(NH_4)_2$, and BHPP, X is $CH_2$, n is 6, $L^1$ is a single bond or is $CH_2$, $L^2$ is selected from the group consisting of NHCO and NH—CS—NH, $R^6$ is selected from the group consisting of UV-chromophores and fluorescent moieties. In a further variation of this embodiment, $L^2$ is NHCO and $R^6$ is phenyl. In still another variation, $R^1$, $R^2$, $R^3$, $R^4$ and $R^5$ are all $PO_3(NH_4)_2$, $PO_3H_2$, or H.

According to yet another embodiment, $R^1$, $R^2$, $R^3$, $R^4$ and $R^5$ are selected from the group consisting of $PO_3H_2$, $PO_3Na_2$, $PO_3(NH_4)_2$, and BHPP, X is $CH_2$, n is 6, $L^1$ is a single bond or is $CH_2$, $L^2$ is NHCO or NHCSNH, and $R^6$ is fluorescein-5-yl. In further variations of this embodiment, $R^1$, $R^2$, $R^3$, $R^4$ and $R^5$ are all $PO_3(NH_4)_2$, $PO_3H_2$, or H.

According to still another embodiment, $R^1$, $R^2$, $R^3$, $R^4$ and $R^5$ are selected from the group consisting of $PO_3H_2$, $PO_3Na_2$, $PO_3(NH_4)_2$, and BHPP, X is $CH_2$, n is 6, $L^1$ is a single bond or is $CH_2$, $L^2$ is NHCO or NHCSNH, and $R^6$ is fluorescein-6-yl. In further variations of this embodiment, $R^1$, $R^2$, $R^3$, $R^4$ and $R^5$ are all $PO_3(NH_4)_2$, $PO_3H_2$, or H.

According to a further embodiment, $R^1$, $R^2$, $R^3$, $R^4$ and $R^5$ are selected from the group consisting of $PO_3H_2$, $PO_3Na_2$, $PO_3(NH_4)_2$, and BHPP, $CH_2CH_2O$, n is 3 or 4, $L^1$ is a single bond or is $CH_2$, $L^2$ is a single bond or $CH_2CH_2CH_2NH$, and $R^6$ is 7-nitro-2-oxa-1,3-diazol-4-yl. In further variations of this embodiment, $R^1$, $R^2$, $R^3$, $R^4$ and $R^5$ are all $PO_3(NH_4)_2$, $PO_3H_2$, or H.

Per one form of this embodiment, $R^5$ is selected from the group consisting of H, benzyl, and 4-methoxybenzyl; X is $CH_2$; n is an integer from 2 to 8; $L^1$ is a single bond or is $CH_2$, $L^2$ is selected from the group consisting of CO—NH, NH—CO, NH—CO—NH, NH—CS—NH, O—CO—NH, and $NH-SO_2$; and $R^6$ is a UV-chromophore or a fluorescent moiety.

In another form, L is NH—CO and $R^6$ is phenyl. Alternatively, L is NH—CS—NH and $R^6$ is fluorescein-5-yl. Per still another form, L is NH—CS—NH and $R^6$ is fluorescein-6-yl.

In another embodiment, $R^1$, $R^2$, $R^3$, $R^4$ and $R^5$ are all $PO_3(NH_4)_2$, X is $CH_2$, n is 5, $L^1$ is $CH_2$, and $L^2$ is NHCO. $R^6$ is selected from the group consisting of UV-chromophores and fluorescent moieties. In one form of this embodiment, $R^6$ is phenyl.

WRITTEN DESCRIPTION

The following definitions are applicable in this written specification:

"Alkane": A linear, branched, or cyclic compound containing hydrogen and carbon connected by single bonds.

"Alkyl": A linear, branched, or cyclic moiety containing hydrogen and carbon connected by single bonds.

"Aryl": A cyclic moiety containing at least one six-carbon ring with three double bonds.

"Benzyl": The chemical moiety that is phenylmethyl.

"BHPP": (Bis(1,2-hydroxymethyl)phenyl)phosphate, the cyclic phosphate ester moiety that contains the 1,5-dihydrobenzo[e][2-oxo-1,3,2-dioxaphosphepan]-2-yl moiety.

"Benzyl acetal": The reaction product of a 1,2-diol with benzaldehyde that includes the structural moiety of 2-phenylmethyl-1,3-dioxolane.

"Chromophore": A chemical moiety which absorbs selected wavelengths of light.

"Cyclohexane ketal": The reaction product of a 1,2-diol with cyclohexanone that includes the structural moiety of 2-(spirocyclohexyl)-1,3-dioxolane.

"Cyclopentane ketal": The reaction product of a 1,2-diol with cyclopentanone that includes the structural moiety of 2-(spirocyclopentyl)-1,3-dioxolane.

"Diethyl ketal": The reaction product of a 1,2-diol with 3-pentanone that includes the structural moiety of 2,2-diethyl-1,3-dioxolane.

"Dimethyl ketal": The reaction product of a 1,2-diol with acetone that includes the structural moiety of 2,2-dimethyl-1,3-dioxolane.

"Fluorescein": A fluorescent compound of the formula $C_{20}H_{12}O_5$.

"Heteroaryl": An aromatic moiety containing at least one five-membered ring with two double bonds or at least one six-membered ring with three double bonds, either of which contains one or more heteroatoms.

"Heteroatom": An atom that is O, N or S.

"4-Methoxybenzyl acetal": The reaction product of a 1,2-diol with 4-methoxybenaldehyde that includes the structural moiety of 2-(4-methoxybenzyl)-1,3-dioxolane.

"Pentacyclic acetal": The reaction product of a 1,2-diol with an aldehyde that includes the structural moiety of the five-membered ring that is 1,3-dioxolane.

"Pentacyclic ketal": The reaction product of a 1,2-diol with a ketone that includes the structural moiety of the five-membered ring that is 1,3-dioxolane.

"Phenyl": A cyclic moiety of the formula $C_6H_5$.

"UV-chromophore": A chemical moiety that absorbs selected wavelengths of ultraviolet light. Exemplary UV-chromophores include, without limitation, aryl and heteroaryl moieties.

"UV-visible-chromophore": A chemical moiety that absorbs selected wavelengths of ultraviolet and visible light.

Referring now to the written specification and the drawings, the present invention will be seen to most generally comprise a myo-inositol derivative compound characterized by the following nominal formula:

Wherein $R^1$, $R^2$, $R^3$ and $R^4$ are identical, and are selected from the group consisting of $PO_3H_2$, $PO_3Na_2$, $PO_3K_2$, $PO_3Li_2$, $PO_3Ca$, $PO_3Mg$, $PO_3(NH_4)_2$, $PO_3(RNH_3)_2$, $PO_3(R_2NH_2)_2$, $PO_3(R_4N)_2$, $PO(OR)_2$, H, COZ and BHPP, where R is benzyl or alkyl of 1 to 6 carbon atoms and Z is an alkyl or arylalky group that provides a cleavable ester protecting group; $R^5$ is selected from the group consisting of H, benzyl, 4-methoxybenzyl, COZ, $PO_3H_2$, $PO_3Na_2$, $PO_3K_2$, $PO_3Li_2$, $PO_3Ca$, $PO_3Mg$, $PO_3(NH_4)_2$, $PO_3(RNH_3)_2$, $PO_3(R_2NH_2)_2$, $PO_3(R_4N)_2$, $PO(OR)_2$, and BHPP, where R is benzyl or alkyl of 1 to 6 carbon atoms and Z is an alkyl or arylalky group that provides a cleavable ester protecting group; X is selected from the group consisting of $CH_2$, $CH_2CH_2O$, and $CH_2CH_2CH_2O$; n is an integer from 1 to 8; $L^1$ is selected from the group consisting of a single bond and $CH_2$; $L^2$ is selected from the group consisting of a single bond, CONH, $CH_2CONH$, $CH_2CH_2CONH$, $CH_2CH_2NHCO$, $CH_2CH_2NHCONH$, $CH_2CH_2NHCSNH$, $CH_2CH_2NHSO_2$, $CH_2CH_2CH_2NHCO$, $CH_2CH_2CH_2NHCONH$, $CH_2CH_2CH_2NHCSNH$, $CH_2CH_2CH_2NHSO_2$, NHCO, NHCONH, NHCSNH, OCONH, $CH_2$, $CH_2CH_2$, $CH_2CH_2O$, $CH_2CH_2S$, $CH_2CH_2NH$, $CH_2CH_2CH_2$, $CH_2CH_2CH_2O$, $CH_2CH_2CH_2S$, $CH_2CH_2CH_2NH$, and NH—$SO_2$; and $R^6$ is selected from the group consisting of UV-visible chromophores, UV-chromophores, fluorescent moieties, and radiolabeled moieties.

The cleavable ester protecting groups comprehend, without limitation, those protecting groups which can be cleaved by treatment with a lipase, according to known techniques.

According to another embodiment of this derivative compound, $R^1$, $R^2$, $R^3$, $R^4$ and $R^5$ are selected from the group consisting of $PO_3H_2$, $PO_3Na_2$, $PO_3(NH_4)_2$, and BHPP, X is $CH_2$ or $CH_2CH_2O$, n is an integer from 2 to 8, $L^1$ is a single bond or is $CH_2$, $L^2$ is selected from the group consisting of a single bond, CONH, NHCO, NHCONH, NHCSNH, OCONH, NHSO_2, $CH_2CH_2CONH$, $CH_2CH_2CH_2NH$, $CH_2CH_2CH_2NHCO$, $CH_2CH_2CH_2NHCONH$, $CH_2CH_2CH_2NHCSNH$, $CH_2CH_2CH_2OCONH$, and $CH_2CH_2CH_2NHSO_2$, and $R^6$ is selected from the group consisting of UV-visible chromophores, UV-chromophores, fluorescent moieties, and radiolabeled moieties. In one variation, $R^6$ is selected from the group consisting of UV-chromophores and fluorescent moieties. In a further variation of this embodiment, X is $CH_2$, n is 6, and $L^2$ is selected from the group consisting of NH—CO and NH—CS—NH.

According to another embodiment, $R^1$, $R^2$, $R^3$, $R^4$ and $R^5$ are selected from the group consisting of $PO_3H_2$, $PO_3Na_2$, $PO_3(NH_4)_2$, and BHPP, X is $CH_2$, n is 6, $L^1$ is a single bond or is $CH_2$, $L^2$ is selected from the group consisting of NHCO and NH—CS—NH, $R^6$ is selected from the group consisting of UV-chromophores. and fluorescent moieties. In a further variation of this embodiment, $L^2$ is NHCO and $R^6$ is phenyl. In still another variation, $R^1$, $R^2$, $R^3$, $R^4$ and $R^5$ are all $PO_3(NH_4)_2$, $PO_3H_2$, or H.

According to yet another embodiment, $R^1$, $R^2$, $R^3$, $R^4$ and $R^5$ are selected from the group consisting of $PO_3H_2$, $PO_3Na_2$, $PO_3(NH_4)_2$, and BHPP, X is $CH_2$, n is 6, $L^1$ is a single bond or is $CH_2$, $L^2$ is NHCO or NHCSNH, and $R^6$ is fluorescein-5-yl. In further variations of this embodiment, $R^1$, $R^2$, $R^3$, $R^4$ and $R^5$ are all $PO_3(NH_4)_2$, $PO_3H_2$, or H.

According to still another embodiment, $R^1$, $R^2$, $R^3$, $R^4$ and $R^5$ are selected from the group consisting of $PO_3H_2$, $PO_3Na_2$, $PO_3(NH_4)_2$, and BHPP, X is $CH_2$, n is 6, $L^1$ is a single bond or is $CH_2$, $L^2$ is NHCO or NHCSNH, and $R^6$ is fluorescein-6-yl. In further variations of this embodiment, $R^1$, $R^2$, $R^3$, $R^4$ and $R^5$ are all $PO_3(NH_4)_2$, $PO_3H_2$, or H.

According to a further embodiment, $R^1$, $R^2$, $R^3$, $R^4$ and $R^5$ are selected from the group consisting of $PO_3H_2$, $PO_3Na_2$, $PO_3(NH_4)_2$, and BHPP, $CH_2CH_2O$, n is 3 or 4, $L^1$ is a single bond or is $CH_2$, $L^2$ is a single bond or $CH_2CH_2CH_2NH$, and $R^6$ is 7-nitro-2-oxa-1,3-diazol-4-yl. In further variations of this embodiment, $R^1$, $R^2$, $R^3$, $R^4$ and $R^5$ are all $PO_3(NH_4)_2$, $PO_3H_2$, or H.

Per one form of this embodiment, $R^5$ is selected from the group consisting of H, benzyl, and 4-methoxybenzyl; X is $CH_2$; n is an integer from 2 to 8; $L^1$ is a single bond or is $CH_2$, $L^2$ is selected from the group consisting of CO—NH, NH—CO, NH—CO—NH, NH—CS—NH, O—CO—NH, and NH—$SO_2$; and $R^6$ is a UV-chromophore or a fluorescent moiety.

In another form, L is NH—CO and $R^6$ is phenyl. Alternatively, L is NH—CS—NH and $R^6$ is fluorescein-5-yl. Per still another form, L is NH—CS—NH and $R^6$ is fluorescein-6-yl.

In another embodiment, $R^1$, $R^2$, $R^3$, $R^4$ and $R^5$ are all $PO_3(NH_4)_2$, X is $CH_2$, n is 5, $L^1$ is $CH_2$, and $L^2$ is NHCO. $R^6$ is selected from the group consisting of UV-chromophores and fluorescent moieties. In one form of this embodiment, $R^6$ is phenyl.

The inventive compounds as contemplated by the present invention include stereoisomers.

EXPERIMENTAL EXAMPLE 1

Derivation of an Exemplary Probe

Figure 1:
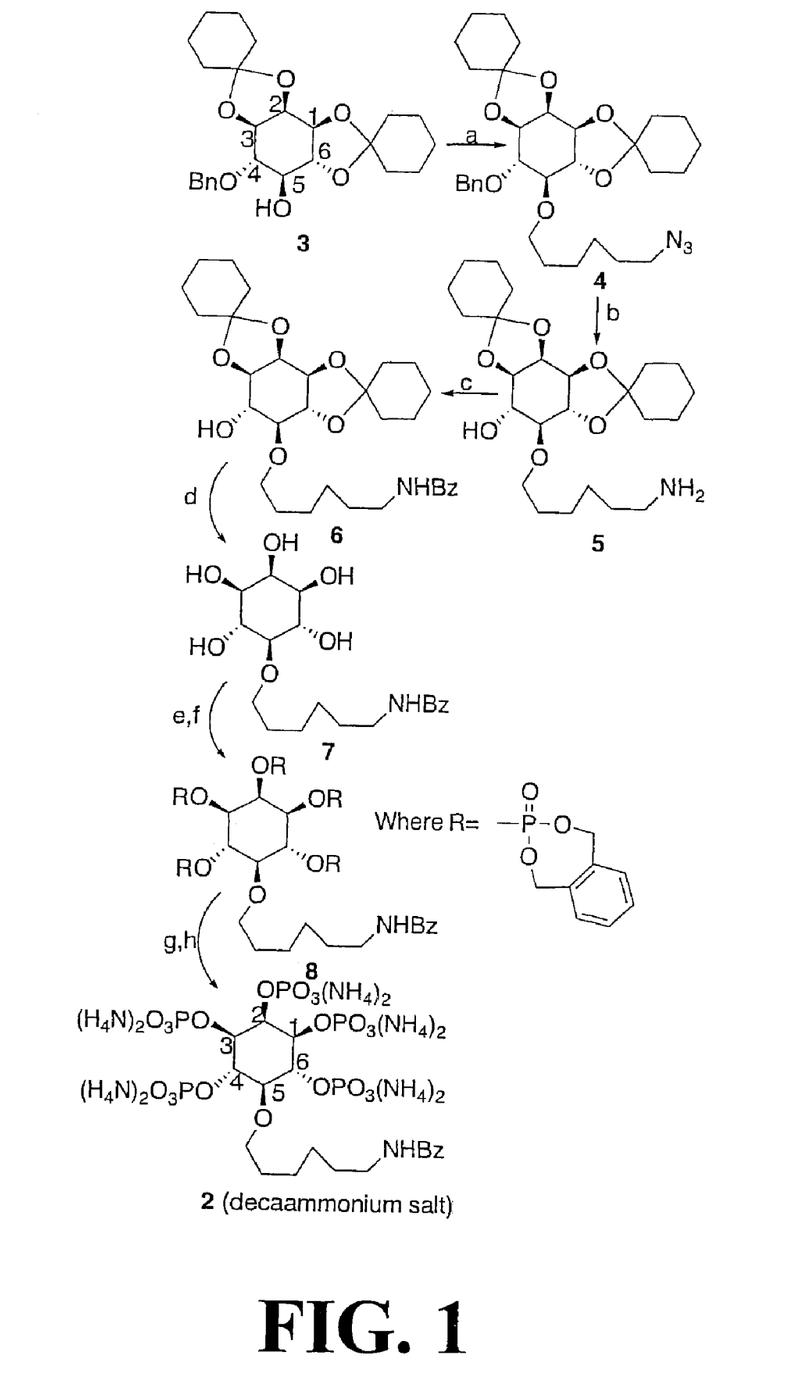
FIG. 1 is a schematic showing the synthesis of an exemplary phytic acid probe (compound 2) according to the instant invention.

Referring now to FIG. 1, derivation of an exemplary compound—namely, 5-O-[6-(benzoylamino)hexyl]-D-myo-inositol-1,2,3,4,6-pentakisphosphate (2) according to the present invention will be better understood.

The compound 4-O-benzyl-1,6:2,3-di-O-cyclohexylidine-myo-inositol 3 was selected as the starting material since it allows for ether-linked derivatization at the 5-position (phytic acid numbering), it positions the linker "meta" to the initial site of reaction (i.e., the 3-position), thus minimizing the chances that the linker (plus chromophore) would interfere with the preferential active site of a 3-phytase, and further simplifies the stereochemical issues via placement of the linker in the meso plane. An ester linkage, by contrast, would be less desirable as being hydrolytically stable and more resistant to phosphatase activity.

Following the procedure of Garegg et al., as published in *Carbohydrate Res.* 1984, 130, 322, the inventors hereof prepared 100 g of the pure isomer 3 of FIG. 1 with flash chromatography followed by recrystallization. The protected myo-inositol 3 was alkylated at the open 5-position using the mesylate of 6-azidohexa-1-ol and sodium hydride in DMF. It was found that moderate heat was necessary to ensure a complete reaction. More specifically, 2.8 grams (70 mmol) of 60% NaH (mineral oil suspension) was added to a solution comprising 15 grams (34.7 mmol) of the compound 3 in 190 ml DMF. The mixture was stirred for 45 minutes and then 1-azzodihexyl 6-O-mesylate (19.2 grams, 86.8 mmol) was added dropwise over a period of 15 minutes. The mixture was thereafter stirred for a further 5 minutes before placing the reaction flask in an oil bath preheated to 60° C. After 18 hours of incubation, the reaction was checked by thin-layer chromatography ("tlc") (Hexanes-EtOAc (4:1), visualization with $H_2SO_4$/EtOH/hot plate) which indicated the complete absence of the compound 3 and the presence of a faster moving product. The reaction mixture was cooled to room temperature and poured into a separatory funnel containing 1.4 L EtOAc. The mixture was washed four times with 400 ml portions of water, once with 300 ml of brine, and the aqueous washes discarded. The organic layer was subsequently dried ($Na_2SO_4$), decanted from the drying agent and concentrated in vacuo to afford the crude resinous product. Subsequent purification was achieved using flash silica gel (400 g) column purification. The column was packed in Hexanes-EtOAc 20:1 and loaded with the crude product (dissolved in 30 ml of the Hexanes-EtOAc 20:1 mixtures). The column was eluted first with the Hexanes-EtOAc 20:1 (2.1 L), then with 17.5:1 (1.85 L) and finally with 15:1 (1.6 L), collecting 125 ml fractions. Pure product was contained in fractions 20-44. These fractions were combined, concentrated in vacuo (aspirator vacuum, 35° C.) to afford a syrup which was co-evaporated from 250 ml of anhydrous dichloromethane. The product was then dried at 0.1 torr at 45° C. for 4 hours to give 17.3 g (89.5% yield).

Simple hydrogenation of the compound 4 over 10% Pd/C reduced the sidechain azide to an amine with concomitant removal of the ring O-benzyl group affording a 55% yield of the product 5. More specifically, a 2 L hydrogenation vessel was charged with 600 ml of a 5:1 mixture of THF:MeOH, 16.5 g (29.7 mmol) of the compound 4, purged with Argon, and 14 g of 10% Pd/C added. The reaction vessel was then hydrogenated on a Parr shaker at 40 PSI for 4 days. The Pd/C was filtered off and the filtrate concentrated to afford 13.45 g of the compound 5 as a resin. To remove traces of MeOH from this product, it was co-evaporated two times from 50 ml portions of anhydrous DCM.

Selective benzoylation of the amino group in 5 was accomplished with benzoyl cyanide in dichloromethane giving a 77% yield of the product 6. Specifically, to a solution comprising the compound 5 (10.2 g, 23.2 mmol) in 160 ml anhydrous DCM was added, dropwise with stirring via an addition funnel, a solution of benzoyl cyanide (3.36 g, 25.63 mmol) in 160 ml of anhydrous DCM. The reaction mixture was stirred for 16 hours, and thereafter 75 ml of saturated aqueous $NaHCO_3$ added, and the mixture stirred for a further 45 minutes. The aqueous wash was discarded and the organic layer dried over $Na_2SO_4$. The drying agent was removed by filtration, and the filtrate concentrated to afford a resin. Purification was achieved using flash silica gel (440 g) column purification. The column was packed in Hexanes-EtOAc 3:2, and loaded with the crude product (dissolved in 20 ml of the Hexanes-EtOAc 1:1 mixture). The column was eluted with the Hexanes-EtOAc (3:2, 1.5 L), collecting 75 ml fractions. Pure product was contained in fractions 21-33. These fractions were combined, concentrated in vacuo (aspirator vacuum, 35° C.) to afford a solid which twice was dissolved in 50 ml of anhydrous dichloromethane, and re-concentrated, dried under vacuum (0.1 torr) at room temperature, to afford 7.4 g (58.6%) of the compound 6.

When compound 6 was subsequently heated in an acetic acid/water mixture at 100° C. for 45 minutes, the 1,6:2,3 cyclohexylidene groups were selectively removed, giving the 5-O-derivitized myo-inositol 7 in 94% yield. More particularly, to a mixture of acetic acid (32 mL) and water (8 mL) was added 3.0 g (5.52 mmol) of the compound 6 and the reaction mixture warmed at 100° C. for 1 hour whereby tlc (Hexanes-EtOAc 1:1) indicated the absence of starting material. The mixture was cooled to room temperature and the solvents removed under 0.1 torr vacuum on a rotary evaporator at ≦35° C. to afford a white solid. This material was co-evaporated four times from 100 mL portions of toluene, and the resultant solid slurried with ethyl ether and collected by filtration. The product was dried in an aberhalden in vacuo (0.1 torr) at 78° C. over $P_2O_5$ for 16 hours to give 2.0 g (94%) of the compound 7 as a white solid, mp 232-236° C.

Through the reaction of the compound 7 with N,N-diethyl-1,5-dihydro-2,4,3-benzodioxaphosphepin-3-amine in the presence of tetrazole, followed by oxidation with m-CPBA, the compound 8 was prepared in 88% yield. More particularly, 1.15 g (16.41 mmol, 10.5 equivalents) tetrazole was added to a stirred solution of the compound 7 (600 mg, 1.56 mmol) in 40 mL of anhydrous MeCN to yield a light suspension. A solution of N,N-diethyl-1,5-dihydro-2,4,3-benzodioxaphosphepin-3-amine (2.6 g, 10.87 mmol, 7 equivalents) in 20 mL of anhydrous acetonitrile was added dropwise with stirring to this suspension. The reaction mixture was stirred for 36 hours. Tlc on silica gel plates (Hexanes-Ethyl Acetate, (3:2)), showed a major non-polar product at $R_f$=0.62, along with base line impurities. When the tlc plate was developed in DCM/MeOH (50:1), the "base line" spot yielded 6-8 faint but distinguishable components, along with the major product (now with an $R_f$ near the solvent front). At this point, 27 ml of 0.5 M iodine in a THF/Pyridine/$H_2O$ (10:5:1) was added. The "iodine tinted" mixture was stirred for 2 hours at room temperature. Tlc of the reaction mixture showed that the major non-polar product with $R_f$=0.62 (elution with Hexanes-Ethyl Acetate (3:2)) to be no longer present, with only a base line spot. Tlc of the reaction mixture in DCM/MeOH (20:1) now showed a major spot of $R_f$=0.67, along with some faint baseline impurities. The reaction was deemed complete and poured into 600 ml of EtOAc. The mixture was washed once with 200 ml of 10% aqueous sodium bisulfite, once with 200 ml of saturated aqueous bicarbonate and finally with 100 ml of brine. The organic layer was dried over anhydrous sodium sulfate and filtered, and the resulting filtrate was concentrated under aspirator vacuum at 35° C. to afford a solid residue. This residue was slurried with 20 ml of acetone and filtered to collect an off-white solid, 440 mg. Tlc, on silica gel, of this solid product revealed it as the major product seen at $R_f$=0.67 in the reaction mixture. This solid was subsequently dissolved in 25 ml of MeOH, and adsorbed in to 5 g of powdered $Na_2SO_4$. The solid was thereafter placed onto a flash silica gel (20 g) column packed in DCM/MeOH (20:1) and eluted, initially with the same for a total of 200 ml, then switching to 10:1, collecting 20 ml fractions. The fractions 3, 4 and 5, containing pure product with the $R_f$=0.67, were combined and concentrated in vacuo to afford a white solid, 150 mg, at 149-152° C. solid transforms to a "glass," then at 250° C. (dec).

$^{31}$P NMR of the compound 8 showed three singlets in a 2:1:2 ratio, consistent with a molecule containing a meso plane and equilibration of chair conformations. Removal of the protecting groups from compound 8 was accomplished by hydrogenation over 5% Pd/C, giving compound 2 as a penta-dihydrogen phosphate which was then directly, without isolation, converted to the decaammonium salt 2 via treatment with ammonium hydroxide. The overall yield for these last two steps was 96%. More specifically, the compound 8 (140 mg, 0.108 mmol) was added to 20 ml of MeOH, the mixture warmed slightly to dissolve, and 3 ml of THF and 4 ml of $H_2O$ added. The reaction vessel was purged with $N_2$, and 200 mg of 5% Pd/C added. The reaction vessel was placed on a Parr shaker and purged with $NH_2$ several times, and thereafter placed under a head pressure of 50 PSI $H_2$. The mixture was hydrogenated for 16 hours at room temperature, following which 1.1 mmol of ammonium hydroxide was added. The mixture was subsequently filtered through celite to remove the catalysts, and the resulting filtrate was concentrated in vacuo (1 torr, 35° C.) to afford a colorless, opaque glass. The crude product was then re-dissolved in distilled water and filtered through a 0.2 micron TEFLON membrane filter, and the filtrate then re-concentrated to give a white solid. This solid product was slurried in $Et_2O$, and filtered to give the compound 2, which compound was then dried under 0.1 torr at room temperature to yield 99 mg (96%) of the final product 2.

$^{31}$P NMR for compound 2 consisted of three singlets at 0.56, 1.19 and 3.12 ppm (integration 2:1:2), consistent with the phosphates at C-1 and C-3 being equivalent, as with the phosphates at C-4 and C-6, and with the singlet at 1.19 ppm (integration one) attributable to the C-2 meso plane phosphate group. The $^1$H NMR spectrum confirmed the structural components, i.e., linker, benzamido and ring methines, for structure 2. Further definitive evidence for 2 was obtained from the mass spectrum. Though a negative ion Maldi mass spectrum did give an [M-H]-ion at m/z 782, determination of an exact mass was not possible. However, the exact mass of 782.0168 (predicted 782.0183), consistent with the desired product 2 anion, was achieved by negative ion electrospray.

EXPERIMENTAL EXAMPLE II 3- and 6-Phytase Assays

Referring now to FIGS. 2 through 5, the aforesaid exemplary probe according to the instant invention (compound 2 of FIG. 1) was employed in assays of 3-phytase and 6-phytase activity. The 3-phytase assay consisted of a solution combining *A. ficuum* 3-phytase (0.27 U) and the penta-ammonium salt of compound 2 (1.2 mM in glycine-HCl buffer 0.2M, pH 2.6, 3 mL). The 3-phytase assay was carried out at 37° C. The 6-phytase assay consisted of a solution combining wheat 6-phytase (0.27 U) and compound 2 (1.2 mM in sodium acetate buffer, 0.2M, pH 5.2, 3 mL). The 6-phytase assay was carried out at 50° C.

Control assays were similarly prepared but lacked the phytase enzyme. Assays were carried out in tinted vials, capped with septa and stirred continuously. Aliquot samples (30 μL) were taken and diluted with methanol-water (58:42, 970 μL) for HPLC analysis over the 24-hour time course of the assay.

Mobile phase (pH 4.0) was prepared by mixing methanol (580 mL), water (420 mL), tetrabutylammonium hydroxide (8 mL), 5N aqueous sulfuric acid (0.5 mL), and 6.4 mM aqueous phytic acid (0.2 mL). HPLC analysis was performed on an analytical HPLC system using a reversed phase column (Hamilton PRP-1, 5 μm, 150×4.6 mm). Compounds were quantified by the external standards method.

Figure 2:
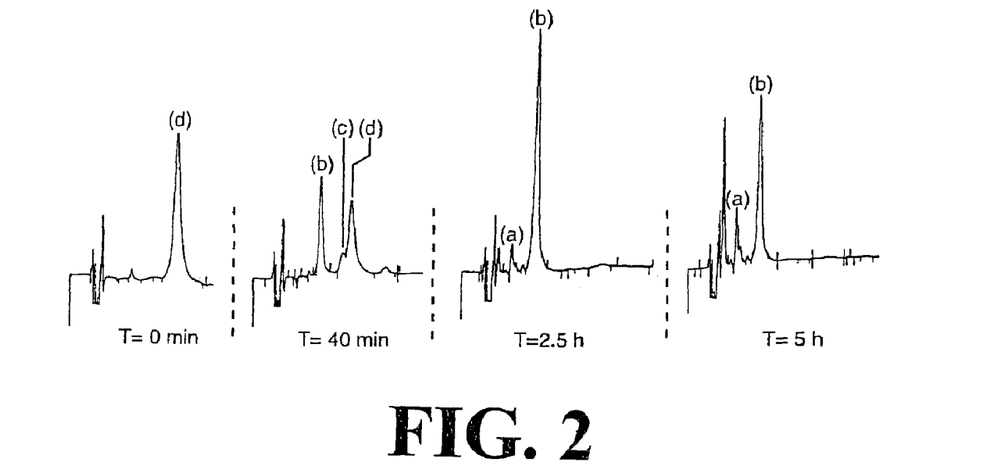
FIG. 2 comprises a series of HPLC chromatograms depicting the sequential dephosphorylation of the phytic acid probe of FIG. 1 by 3-phytase.
Figure 3A:
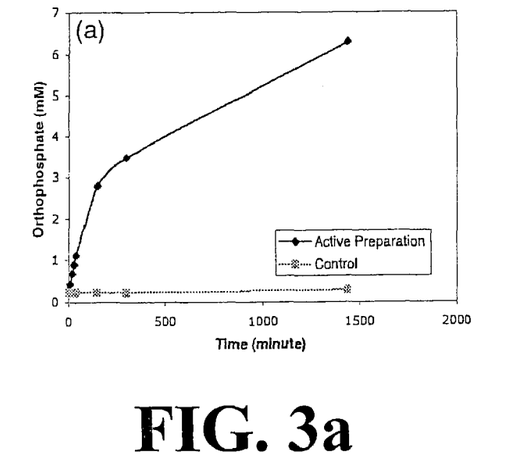
FIGS. 3a through 3c show the kinetics of ortho-phosphate release upon 3-phytase-catalysed dephosphorylation of the phytic acid probe of FIG. 1 (FIG. 3a), the accumulation and eventual decline of the triphosphate product, indicating the rate-limiting step (FIG. 3b), and a progress curve showing the release of ortho-phosphate upon dephosphorylation of the phytic acid probe of FIG. 1 (FIG. 3c)
Figure 3B:
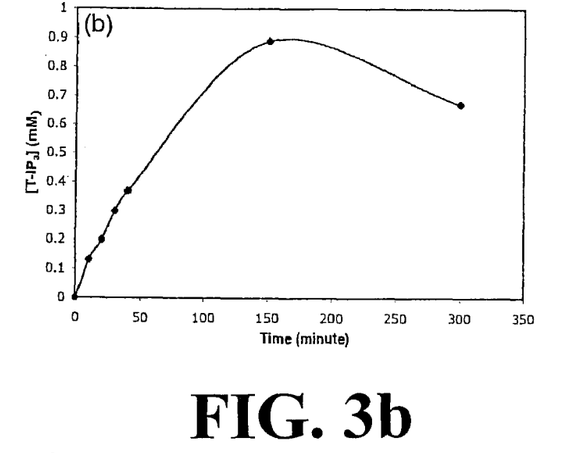
Figure 3C:
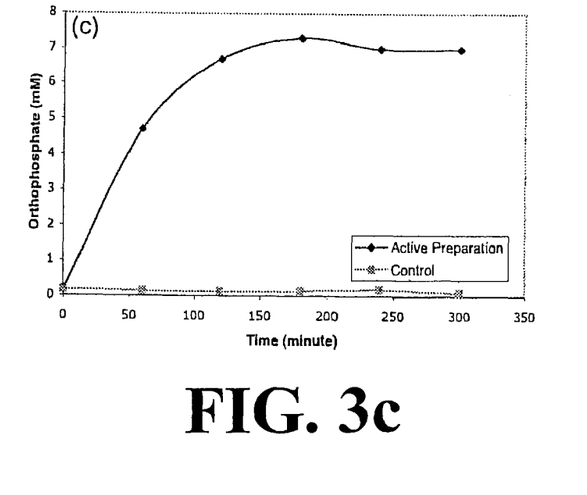
Figure 4:
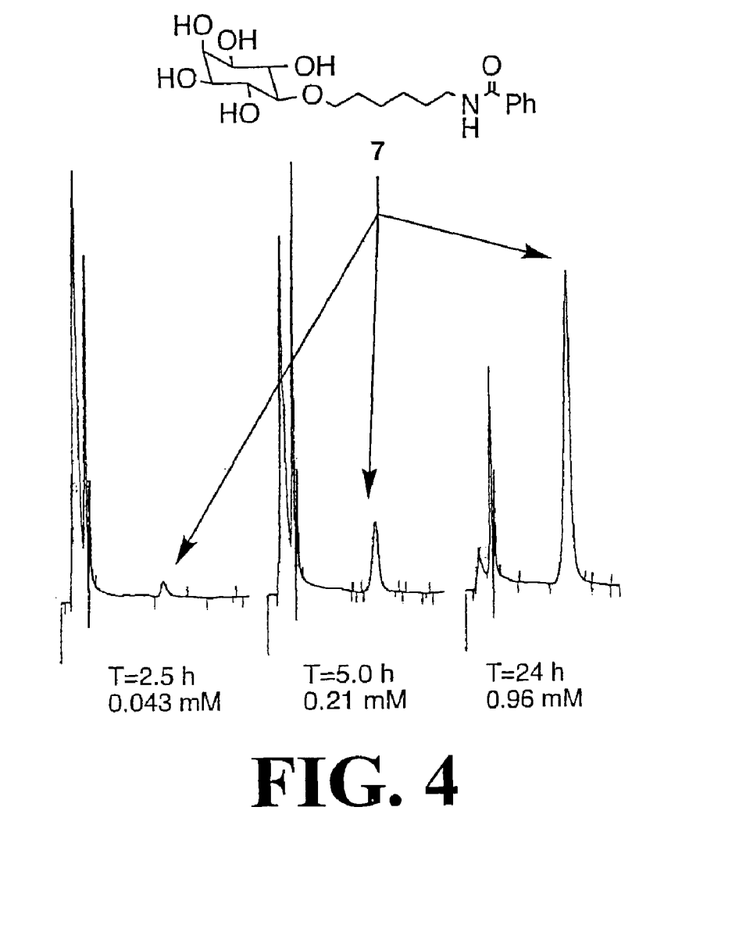
FIG. 4 shows HPLC chromatograms illustrating the appearance of T-myo-inositol (compound 7 of FIG. 1) from the complete dephosphorylation of the phytic acid probe of FIG. 1.
Figure 5:
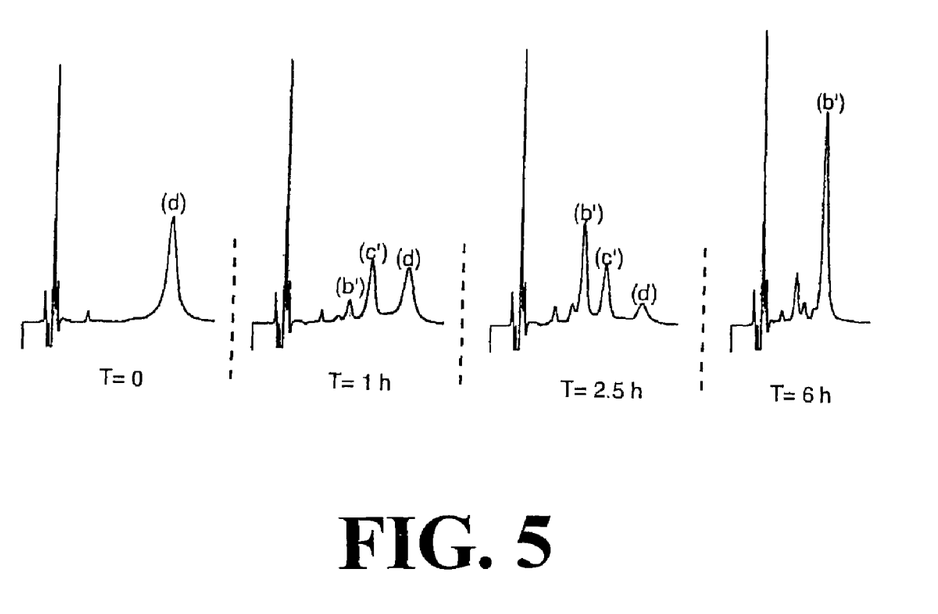
FIG. 5 shows a series of HPLC chromatograms depicting the sequential dephosphorylation of the phytic acid probe of FIG. 1 by 6-phytase.

Typical assay output for 3-phytase is shown in FIG. 2 wherein the disappearance of compound 2 (peak d) and the sequential appearance and decline of the analogous tetra-phosphate (peak c), the triphosphate (peak b), and the mono-phosphate (peak a) are observed with increasing incubation time. The concomitant release of ortho-phosphate may also be monitored for compound 2 (FIG. 3a) and myo-$IP_6$ (FIG. 3c). The accumulation of the triphosphate (peak b in FIG. 2 and FIG. 3b) and the lack of a significant peak for the diphosphate indicate that the rate limiting step of the production of compound 7 from compound 2 is conversion of triphosphate to diphosphate. After 24 hours of incubation, compound 2 is completely converted to compound 7 in the presence of 3-phytase (FIG. 4). In contrast, no conversion was seen in the enzyme free control. Neither in the assay nor in the control is there any evidence of amide bond cleavage that would separate the UV chromophore from the phytic acid core. In other words, no benzoic acid could be detected by HPLC. Analogous assay output for 6-phytase is shown in FIG. 5, which demonstrates that compound 2 serves equally well as a substrate for 6-phytase.

It will be appreciated from the above disclosure that the present invention improves upon the prior art by providing probes which act as optically detectable substrates in a specific, sensitive, and quantitative assay of phytase enzyme activity.

Of course, the foregoing is merely illustrative of the present invention, and those of ordinary skill in the art will appreciate that many additions and modifications to the present invention, as set out in this disclosure, are possible without departing from the spirit and broader aspects of this invention as defined in the appended claims.

All publications identified above are hereby incorporated herein by reference in their entireties.

The invention claimed is:

1. A myo-inositol derivative compound of the following nominal formula:

Wherein $R^1$, $R^2$, $R^3$ and $R^4$ are identical, and are selected from the group consisting of $PO_3H_2$, $PO_3Na_2$, $PO_3K_2$, $PO_3Li_2$, $PO_3Ca$, $PO_3Mg$, $PO_3(NH_4)_2$, $PO_3(RNH_3)_2$, $PO_3(R_2NH_2)_2$, $PO_3(R_4N)_2$, $PO(OR)_2$, H, COZ and BHPP, where R is benzyl or alkyl of 1 to 6 carbon atoms and Z is an alkyl or arylalky group that provides a cleavable ester protecting group;

$R^5$ is selected from the group consisting of H, benzyl, 4-methoxybenzyl, COZ, $PO_3H_2$, $PO_3Na_2$, $PO_3K_2$, $PO_3Li_2$, $PO_3Ca$, $PO_3Mg$, $PO_3(NH_4)_2$, $PO_3(RNH_3)_2$, $PO_3(R_2NH_2)_2$, $PO_3(R_4N)_2$, $PO(OR)_2$, and BHPP, where R is benzyl or alkyl of 1 to 6 carbon atoms and Z is an alkyl or arylalky group that provides a cleavable ester protecting group;

X is selected from the group consisting of $CH_2$, $CH_2CH_2O$, and $CH_2CH_2CH_2O$;

n is an integer from 1 to 8;

$L^1$ is a single bond or $CH_2$;

$L^2$ is selected from the group consisting of a single bond, CONH, $CH_2CONH$, $CH_2CH_2CONH$, $CH_2CH_2NHCO$, $CH_2CH_2NHCONH$, $CH_2CH_2NHCSNH$, $CH_2CH_2NHSO_2$, $CH_2CH_2CH_2NHCO$, $CH_2CH_2CH_2NHCONH$, $CH_2CH_2CH_2NHCSNH$, $CH_2CH_2CH_2NHSO_2$, NHCO, NHCONH, NHCSNH, OCONH, $CH_2$, $CH_2CH_2$, $CH_2CH_2O$, $CH_2CH_2S$, $CH_2CH_2NH$, $CH_2CH_2CH_2$, $CH_2CH_2CH_2O$, $CH_2CH_2CH_2S$, $CH_2CH_2CH_2NH$, and $NH-SO_2$; and $R^6$ is selected from the group consisting of UV-visible chromophores, UV-chromophores, fluorescent moieties, and radiolabeled moieties.

2. The compound of claim 1, wherein $R^1$, $R^2$, $R^3$, $R^4$ and $R^5$ are selected from the group consisting of $PO_3H_2$, $PO_3Na_2$, $PO_3(NH_4)_2$, and BHPP, X is $CH_2$ or $CH_2CH_2O$, n is an integer from 2 to 8, $L^2$ is selected from the group consisting of a single bond, CONH, NHCO, NHCONH, NHCSNH, OCONH, $NHSO_2$, $CH_2CH_2CONH$, $CH_2CH_2CH_2NH$, $CH_2CH_2CH_2NHCO$, $CH_2CH_2CH_2NHCONH$, $CH_2CH_2CH_2NHCSNH$, $CH_2CH_2CH_2OCONH$, and $CH_2CH_2CH_2NHSO_2$.

3. The compound of claim 2, wherein $R^6$ is selected from the group consisting of UV-chromophores and fluorescent moieties.

4. The compound according to claim 2, X is $CH_2$, n is 6, $L^1$ is a single bond, and $L^2$ is selected from the group consisting of NHCO and NHCSNH.

5. The compound of claim 4, wherein $L^2$ is NHCO and $R^6$ is phenyl.

6. The compound of claim 5, wherein $R^1$, $R^2$, $R^3$, $R^4$ and $R^5$ are all $PO_3(NH_4)_2$.

7. The compound of claim 5, wherein $R^1$, $R^2$, $R^3$, $R^4$ and $R^5$ are all $PO_3H_2$.

8. The compound of claim 5, wherein $R^1$, $R^2$, $R^3$, $R^4$ and $R^5$ are all H.

9. The compound of claim 2, wherein X is $CH_2$, n is 6, $L^1$ is a single bond, $L^2$ is NHCO or NHCSNH, and $R^6$ is fluorescein-5-yl.

10. The compound of claim 2, wherein X is $CH_2$, n is 6, $L^1$ is a single bond, $L^2$ is NHCO or NHCSNH, and $R^6$ is fluorescein-6-yl.

11. The compound of claim s 9 or 10, wherein $R^1$, $R^2$, $R^3$, $R^4$ and $R^5$ are $PO_3(NH_4)_2$.

12. The compound of either of claims 9 or 10, wherein $R^1$, $R^2$, $R^3$, $R^4$ and $R^5$ are $PO_3H_2$.

13. The compound of claim 9 or 10, wherein $R^1$, $R^2$, $R^3$, $R^4$ and $R^5$ are all H.

14. The compound of claim 2, wherein X is $CH_2CH_2O$, n is 3 or 4, $L^2$ is a single bond or $CH_2CH_2CH_2NH$, and $R^6$ is 7-nitro-2-oxa-1,3-diazol-4-yl.

15. The compound of claim 14, wherein $R^1$, $R^2$, $R^3$, $R^4$ and $R^5$ are $PO_3(NH_4)_2$.

16. The compound of claim 14, wherein $R^1$, $R^2$, $R^3$, $R^4$ and $R^5$ are $PO_3H_2$.

17. The compound of claim 14, wherein $R^1$, $R^2$, $R^3$, $R^4$ and $R^5$ are H.

18. The compound of claim 1, wherein $R^1$, $R^2$, $R^3$, $R^4$ and $R^5$ are all $PO_3(NH_4)_2$, X is $CH_2$, n is 5, $L^1$ is $CH_2$, and $L^2$ is NHCO.

19. The compound of claim 18, wherein $R^6$ is phenyl.

* * * * *

UNITED STATES PATENT AND TRADEMARK OFFICE
CERTIFICATE OF CORRECTION

PATENT NO. : 7,741,506 B2  Page 1 of 1
APPLICATION NO. : 11/982811
DATED : June 22, 2010
INVENTOR(S) : Berry It is certified that error appears in the above-identified patent and that said Letters Patent is hereby corrected as shown below:

In Col. 12, line 15, please delete "of claims" and insert --of either of claims--.

Signed and Sealed this

Tenth Day of August, 2010

David J. Kappos
*Director of the United States Patent and Trademark Office*